United States Patent [19]

Shearer et al.

[11] Patent Number: 4,656,254
[45] Date of Patent: Apr. 7, 1987

[54] METHOD OF PREPARING ALPHA-1-PROTEINASE INHIBITOR AND ANTITHROMBIN III

[75] Inventors: Michael A. Shearer, Suisun; Pamela K. Sasagawa, Emeryville; Ronald H. Hein, Walnut Creek, all of Calif.

[73] Assignee: Miles Laboratories, Inc., Elkhart, Ind.

[21] Appl. No.: 803,184

[22] Filed: Dec. 2, 1985

[51] Int. Cl.$^4$ .......................... C07K 3/28; C07K 3/20; C07K 15/06
[52] U.S. Cl. ................................... 530/393; 424/101; 514/8; 514/21; 530/380; 530/392; 530/395; 530/830
[58] Field of Search .................... 424/101; 260/112 B; 530/380, 392, 393, 395, 830; 514/8, 21

[56] References Cited

U.S. PATENT DOCUMENTS

| | | | |
|---|---|---|---|
| 3,842,061 | 10/1974 | Andersson et al. | 424/101 X |
| 4,379,087 | 4/1983 | Coan et al. | 424/101 X |
| 4,439,358 | 3/1984 | Coan et al. | 424/101 X |
| 4,440,679 | 4/1984 | Fernandes et al. | 424/101 X |

OTHER PUBLICATIONS

Vox Sang. 36, 281–293 (1979), Wickerhauser et al.
Preparative Biochemistry 5(4), 333–348 (1975), Glaser et al.
Analytical Biochemistry, 124, 364–371 (1982), Glaser et al.

*Primary Examiner*—Howard E. Schain
*Attorney, Agent, or Firm*—Pamela A. Simonton; Lester E. Johnson

[57] ABSTRACT

There is disclosed an improved method for separating one of alpha-1-proteinase inhibitor (also known as alpha-1 antitrypsin) and antithrombin-III from an aqueous solution of plasma proteins containing the same, such as from Cohn Fraction IV-1, Cohn Fraction IV, reworks of Cohn Fraction IV and IV-1, Cohn Effluent II & III and Cohn Effluent I. The method includes the steps of first holding an aqueous solution of plasma proteins containing one of alpha-1-proteinase inhibitor and antithrombin-III in a relatively large volume of buffer solution as solvent and at a pH adjusted to be relatively basic when compared to conditions heretofore known, and at a temperature in the range of from 2°–50° C. for a period of about 0.2–24 hours. Following the above treatment, alpha-1-proteinase inhibitor and antithrombin-III are obtained by applying conventional techniques to the resulting solution. Accordingly, the solution is then mixed with a polyalkylene glycol, e.g. polyethylene glycol, in the range of from as low as 8% to as high as 23% (w/v) based on volume of solution to selectively precipitate unwanted proteins. The alpha-1-proteinase inhibitor is then separated from the supernatant solution by adsorption on an anion exchange resin or by precipitation by further addition of a polyalkylene glycol, e.g. polyethylene glycol. The method of the invention provides an improvement in the yield of alpha-1-proteinase inhibitor.

18 Claims, No Drawings

METHOD OF PREPARING ALPHA-1-PROTEINASE INHIBITOR AND ANTITHROMBIN III

BACKGROUND OF THE INVENTION

1. Field of the Invention

This invention relates to and has among its objects the provision of an improved method for separating one of alpha-1-proteinase inhibitor (PI) and antithrombin-III (AT-III) from blood plasma or blood plasma fractions. Further objects of the invention will be evident from the following description wherein parts and percentages are by weight unless otherwise specified.

2. Description of the Prior Art

Alpha-1-proteinase inhibitor is a glycoprotein having molecular weight of 54,000. The protein consists of a single polypeptide chain to which several oligosaccharide units are covalently bound. Human PI has a role in controlling tissue destruction by endogenous serine proteinases. A genetic deficiency of PI, which accounts for 90% of the trypsin inhibitory capacity in blood plasma, has been shown to be associated with premature development of pulmonary emphysema. The degradation of elastin associated with emphysema probably results from a local imbalance of elastolytic enzymes and the naturally occurring tissue and plasma proteinase inhibitors. PI rapidly inhibits human pancreatic and leukocyte elastases (*Biochem. Biophys. Res. Comm.*, Vol. 72, No. 1, pages 33–39, 1976; ibid. Vol. 88, No. 2, pages 346–350, 1979).

A number of methods have been employed to isolate PI from the blood plasma. A majority of these methods are directed to laboratory scale isolation while others pertain to production on a commercial level.

Pannell et al., *Biochemistry*, Vol. 13, pages 5439–5445, (1974), employed a process wherein albumin-poor blood plasma was pooled and fractionated with solid ammonium sulfate (0.60–0.80 saturation). The precipitate resulting was solubilized and dialyzed and applied to a column of DEAE-cellulose. The fraction of PI eluting in the 0.05–0.15M NaCl linear gradient is pooled, concentrated, and dialyzed, and then applied again to a column of DEAE-cellulose. The PI fraction eluting in the linear gradient from 0.05–0.20M NaCl was collected, pooled, and concentrated to give PI.

In the method of Saklatvala et al., *Biochem. J.*, Vol. 157, pages 339–351 (1976), human plasma was fractionated using ammonium sulfate (80% saturation) to give a precipitate, which was dissolved, dialyzed and chromatographed on DEAE-cellulose. The 0.5M NaCl extract was applied to a concanavalin-A-Sepharose column. The alpha-D-methyl glucopyranoside eluate was concentrated and applied again to a DEAE-cellulose column. The 0.0–0.2M NaCl eluate contained PI.

Fifty percent saturated ammonium sulfate precipitation was used by Musiani et al., *Biochem.*, Vol. 15, pages 798–804 (1976) to separate a PI-rich fraction that was solubilized and then subjected to successive chromatographic steps using DEAE ion exchanger, concanavalin A-Sepharose, Sephadex G-100, and an immunoadsorbent column to yield purified PI.

A large scale purification of PI from human plasma was disclosed by Kress et al., *Preparative Biochemistry*, Vol. 3, No. 6, pages 541–552 (1973). The precipitate from the 80% ammonium sulfate treatment of human plasma was dialyzed and chromatographed on DEAE-cellulose. The concentrate obtained was again dialyzed and gel filtered on Sephadex G-100. The PI-containing fractions were chromatographed twice on DE-52 cellulose to give PI. Glaser et al., ibid., Vol. 5, No. 4, pages 333–348 (1975) isolated PI from Cohn Fraction IV-1 in 30% overall yield. Dissolved IV-1 was chromatographed on DEAE-cellulose, QAE-Sephadex, concanavalin A-Sepharose, and G-150 Sephadex to give PI.

An integrated plasma fractionation system based on polyethylene glycol (PEG) was disclosed by Hao et al., *Proceedings of the International Workshop on Technology for Protein Separation and Improvement of Blood Plasma Fractionation*, held Sept. 7–9, 1977, Reston, Va. In the published method Cohn cryoprecipitate was mixed with PEG in an amount of 40 grams per liter (g/l). All operations were conducted at 5° C.

After stirring for 60 minutes, the first fraction was removed by centrifugation. An additional 60 g/l of PEG was added to the supernate (final concentration approximately 10%). Prothrombin complex (PTC) was then extracted from the 10% PEG supernate by batchwise adsorption on DEAE cellulose, and an additional 100 g/l of PEG was added to obtain the 10–20% PEG precipitate. The four fractions thus obtained were 0–4% PEG precipitate, 4–10% PEG precipitate, 10–20% PEG precipitate and 20% PEG supernate, and were designated as Fractions A, B, C and D, respectively. It should be pointed out that these PEG concentrations were based on the original volume of cryosupernate.

The distribution of proteins in the four PEG fractions was as follows: Fibrinogen was the dominant protein in Fraction A with albumin being the major contaminant. Most of the contaminating albumin in Fractions A, B and C resulted from coprecipitation and/or entrapment of supernate since albumin by itself did not precipitate under these conditions. Fraction B was rich in palsminogen, C3 component of complement, IgG and IgM. In addition, virtually all of the beta-lipoproteins were present in this fraction. Fraction C contained appreciable quantities of alpha$_2$macroglobulin, IgA and was rich in prothrombin and other coagulation factors which constitute the so-called prothrombin complex. However, the authors found that better yields of PTC could be obtained from the 10% PEG supernate rather than from the 10–20% PEG precipitate. Fraction D was dominated by albumin but also contained all of the alpha-1-acid glycoprotein as well as most of the PI, antithrombin III (AT III), ceruloplasma ($C_p$), haptoglobin, transferrin ($T_f$) and Cl esterase inhibitor (Cl inhib.). Several additional proteins were also isolated from Fraction D including prealbumin (PA), retinol binding protein (RBP), transcortin, and angiotensinogen. In general, most of the smaller proteins were in Fraction D.

Coan and Brockway, U.S. Pat. Nos. 4,379,087 and 4,439,358, disclose a method for separating alpha-1-proteinase inhibitor from a blood plasma fraction, e.g. Cohn Fraction IV-1, by providing an aqueous solution of the blood plasma fraction and holding such solution at a pH of about 6.5–8.5 and at a temperature of about 2°–50° C. for a period of about 0.2–24 hours, mixing the solution with an amount of polycondensed polyglycol, for example polyethylene glycol, in the range of about 8–10% to about 23% (wt/vol.), based on volume of solution, at a pH in the range of from about 4.6 to about 7.5 wherein the range of amount of polycondensed polyglycol increases about 2–3% per 0.5 increase in pH. In a preferred embodiment, there is used in the patented method about 10–15 g of polycondensed polyglycol per 100 ml of aqueous solution containing Cohn Fraction IV-1 at a pH in the range of 4.6–5.7, the ratio of parts of polycondensed polyglycol to parts of blood plasma fraction being from about 2:1 to 1:1. The alpha-1-proteinase inhibitor is separated from the resulting mixture by cemtrifuging the mixture from the polycondensed polyglycol treatment and recovering the supernatant solution, contacting the resulting supernatant solution with an anion exchange resin at a pH of about 5.5–8.6, and selectively eluting the alpha-1-proteinase inhibitor from the resin. Alternatively, the alpha-1-proteinase inhibitor may be separated by the further addition of polycondensed polyglycol to precipitate alpha-1-proteinase inhibitor from the mixture following the initial centrifugation of the mixture.

When alpha-1-proteinase inhibitor is manufactured, starting with Fraction IV-1 paste, as outlined by Coan et al (above), the average yeild in the Fr. IV-1 suspension is approximately 18% from starting pooled plasma. Precipitation of the PEG Intermediate Purity Paste yields only 8%. Additional losses are also incurred during chromatographic purification and pasteurization. This gives a final container yield of only 4–6% from pooled plasma.

Work completed by Glaser et al (*Anal. Biochem.*, 124, 364–371 [1982]) showed that Cohn Fraction IV-1 contained 30% of all plasma alpha-1-proteinase inhibitor. This low yield has been historically attributed to the denaturation of the Alpha-1-molecule during the precipitation of Fraction IV-1. This precipitation occurs at an alcohol concentration of approximately 21% and a pH of 5.2.

Because of the potential demand for this product in the marketplace, and the high cost of manufacturing, this yield of only about 4–6% is commercially unacceptable. Thus, there exists a need for improvement in the methods for isolating and separating alpha-1-proteinase inhibitor from sources containing the same in order to obtain a higher yield.

Antithrombin-III (AT-III) has been prepared from plasma or Cohn Fraction IV-1 in a 5-step method consisting of: (a) partial purification by precipitating unwanted proteins using polyethylene glycol (PEG); (b) solution of AT-III from the PEG supernatant by batch adsorption and elution on heparin-sepharose; (c) concentrating and desalting the eluted AT-III by ultrafiltration; (d) pasteurization of AT-III by heating the concentrate for 10 hours at 60° C. in the presence of 0.5M sodium citrate at pH 7.5; and (e) sterile filtration, filling and lyophilization. [C. A. Wickerhauser et al, *Vox Sang.*, 36, 281–293 (1979)].

L.-O. Anderson et al, U.S. Pat. No. 3,842,061 disclose a method for isolating AT-III from AT-III containing blood materials, e.g. plasma, comprising contacting the AT-III containing material with a water-insoluble cross-linked sulfated polysaccharide gel matrix adsorbing agent to adsorb the AT-III and then separating AT-III from the adsorbing agent.

SUMMARY OF THE INVENTION

By investigating the solution chemistry of Fr. IV-1 beginning with increasing the volume of the dissolving buffer to see if the larger volume would enhance dissolving, we observed an increase in overall yield of PI and also that the pH of the dissolving buffer did not decrease as much after addition of the paste. Upon further examining the effect pH on recoverable yield by increasing the pH of the dissolving buffer, more PI was recovered from Fr. IV-1 suspension than was previously thought available. Thus, we discovered that the pH and volume of the dissolving buffer used was more critical than previously thought. The Coan process was performed at approximately the same pH and volume as the earlier work of Glaser. By increasing the pH and volume of the dissolving buffer we were above to recover approximately 50% of the alpha-1-found in pooled plasma in the Fraction IV-1 suspension leading to an overall recovery of approximately 30% in the final container. This represents an increase in yield of over 500% from the original Coan method.

Further, we discovered that by dissolving Fraction IV-1 under the conditions described above followed by separating AT-III by following substantially the procedure of Andersson et al, U.S. Pat. No. 3,842,061, we obtained an increase in yield of about 150–200% over the yield starting from Fraction IV-1 dissolved in a lower amount of buffer according to the conventional method(s).

Briefly, the present invention is an improved method for separating alpha-1-proteinase inhibitor (also known in the literature as "alpha-1 antitrypsin") and antithrombin-III from aqueous solution containing the same, such as blood plasma and blood plasma fractions, in a higher yield and purity than has been disclosed heretofore. First, the plasma fraction is dissolved in from 20 to 100 volumes of a physiologically acceptable buffer and the pH is adjusted to about 9.0 to 11.0. Then, the PI and/or AT-III is separated by conventional techniques using a precipitating agent or adsorbing agent.

In one particular aspect the invention described herein is, in a method for separating antithrombin-III from an aqueous solution of plasma proteins containing antithrombin-III which comprises the steps of:
 (a) contacting an aqueous solution of one of the group of blood plasma and a blood plasma fraction which contains antithrombin-III with a water-insoluble, cross-linked sulfated polysaccharide gel matrix adsorbing agent to adsorb antithrombin-III,
 (b) eluting antithrombin-III from the adsorbing agent from step (a), and
 (c) recovering antithrombin-III from the eluant from step (b),
the improvement which comprises:
 (1) providing for use in step (a) an aqueous solution of the one of the blood plasma and blood plasma fraction dissolved in from 20 to 100 volumes of buffer-solution per weight of the plasma or plasma fraction used, and
 (2) prior to use in step (a), adjusting one of the buffer solution and the resulting aqueous solution of the blood plasma and blood plasma fraction from step (1) to render the pH of the resulting solution at from 9.0 to 11.0.

In another particular aspect, the invention described herein is, in a method for separating alpha-1-proteinase inhibitor from an aqueous solution of plasma proteins containing alpha-1-proteinase inhibitor which comprises the steps of:
 (a) contacting an aqueous solution of one of the group of blood plasma and a blood plasma fraction which contains alpha-1-proteinase inhibitor with from about 8% to about 23% (w/v), based on volume of aqueous solution, of polycondensed polyalkylene glycol, at a temperature of about 2° C. to about 50° C. for a period of 0.2–24 hours to selectively precipitate unwanted proteins from the aqueous solutions without precipitating alpha-1-proteinase inhibitor from the aqueous solution to obtain a mixture containing alpha-1-proteinase inhibitor free of unwanted proteins, (b) recovering the mixture from step (a), and
(c) separating alpha-1-proteinase inhibitor from the mixture recovered in step (b), the improvement which comprises:

(1) providing for use in step (a) an aqueous solution of the one of the blood plasma and blood plasma fraction dissolved in from 20 to 100 volumes of buffer solution per weight of plasma or plasma fraction used, and (2) prior to use in step (a) adjusting the pH of one of the buffer solution and the resulting aqueous solution of the blood plasma and blood plasma fraction to render the pH of the resulting solution at from 9.0 to 11.0.

The starting source of alpha-1-proteinase inhibitor and antithrombin-III in the method according to the present invention is blood plasma or a blood plasma fraction containing at least one of alpha-1-proteinase inhibitor and antithrombin-III selected from the group consisting of Cohn Fraction IV-1, Cohn Fraction IV, reworks of Cohn Fraction IV and IV-1, Cohn Effluent II+III, Cohn Effluent I, and cryosupernatant solution.

The primary advantage of the method according to the present invention is a higher recovery of PI or AT-III, when compared with the yield of PI or AT-III obtained by many methods reported in the prior art, in terms of yield from the total amount of PI or AT-III in plasma.

Another advantage is the purity of the PI or AT-III obtained by the method according to the present invention in that this method allows for enhanced separation of other plasma proteins which in prior art methods frequently are recovered along with PI or AT-III as unwanted contaminants.

DESCRIPTION OF THE PREFERRED EMBODIMENTS

As mentioned above, the starting material for the method according to the present invention is blood plasma or a blood plasma fraction containing at least one of alpha-1-proteinase inhibitor and antithrombin-III. Preferably, the aqueous solution containing PI is selected from the group consisting of Cohn Fraction IV-1, Cohn Effluent II+III, Cohn Effluent I, and cryosupernatant solution. Cohn Fraction IV-1, Cohn Effluent II+III and Cohn Effluent I may be obtained by fractionating blood plasma according to the Cohn ethanol fractionation technique or its modifications. See, for example, E. J. Cohn et al, *J. Amer. Chem. Soc.*, 68, 459 (1946); E. J. Cohn, U.S. Pat. No. 2,390,074; Oncley et al, *J. Amer. Chem. Soc.*, 71, 541 (1949); and "The Plasma Proteins", second edition, Volume III, pages 548–550, Academic Press, New York, N.Y. (1975). Cryosupernatant solution may be obtained by thawing fresh frozen plasma at not more than 5° C., removing the remaining precipitate (referred to as "cryoprecipitate") by conventional means, usually centrifugation, and retaining the supernatant solution ("cryosupernatant solution") for use in the method according to the present invention. See, for example, G. Mitra et al, U.S. Pat. No. 4,386,068. More preferably, the aqueous solution containing PI or AT-III used as the starting material is selected from Cohn Fraction IV-1, Cohn Effluent II+III and Cohn Effluent I. Most preferably, the starting aqueous solution containing PI or AT-III is Cohn Fraction IV-1. In the following description, emphasis is directed to Cohn Fraction IV-1 by way of illustration but without limitation.

The first step in the method according to the present invention is to obtain an aqueous solution of the plasma or plasma fraction in a relatively large volume of buffer solution as solvent. By referring to Example 1 in the Coan patents (U.S. Pat. Nos. 4,379,087 and 4,439,358), it will be noted that the patented method discloses the use of about 8 to 10 volumes of buffer solution based on amount (weight) of Fraction IV-1 and holding the resulting solution at a pH of about 6.5–8.5.

According to the present invention, one aspect of the improvement of the invention requires the use of from 20 to 100 volumes, more preferably from 20 to 50 volumes, still more preferably 20–30 volumes, most preferably 24 volumes, of buffer solution per weight of starting plasma or plasma fraction. Although the use of any physiologically compatible buffer solution for use at the pH range defined according to the method of this invention may be used, the use of tris-(hydroxymethyl)aminomethane (TRIS) is preferred. A physiologically acceptable salt, for example, sodium chloride, may be added to the buffer to provide a concentration in the range of 0.0M to 0.20M in the resulting aqueous solution of the plasma or plasma fraction, representative of which is Cohn Fraction IV-1.

The other aspect of the improvement of the invention requires adjusting the pH of one of the buffer solution and the resulting aqueous solution of the blood plasma and blood plasma fraction, representative of which is IV-1, to render the pH of the resulting solution at from 9.0 to 11.0. This adjustment may be achieved by adding sufficient base, for example sodium hydroxide in pellet form or in aqueous solution, to the initial buffer solution or to an initial solution of the plasma or plasma fraction in the initial buffer solution. Alternatively, for reasons of convenience, this pH adjustment may be achieved by adding sufficient sodium hydroxide to the initial buffer solution to obtain a pH of from 10.0 to 11.0. The pH of the resulting aqueous solution of Cohn Fraction IV-1 in the initial buffer solution having the preferred pH is from 9.0 to 10.5.

Although the time and temperature at which the resulting aqueous solution of Fr. IV-1 is held is not considered critical, there yet exists the inverse relationship between time and temperature such that, for each 10° C. rise in temperature, the hold time should decrease by half with the preferred conditions being as described in the Coan procedure, namely, about 0.5 hour at about 45° C. or about 8 hours at about 5° C. As a practical matter, the holding conditions in the practice of the improvements according to this invention include holding the resulting aqueous solution of Fr. IV-1 in 24 volumes of buffer and having a pH of 9.0 to 10.0 for about 2–3 hours, e.g. 2.5 hours, at about 2° C. to 10° C., e.g. at 5° C., followed by about 0.5–2 hours, e.g. 1–1.5 hours, at 30°–45° C.

Fraction IV-1 paste may be used directly or it may first be treated to remove lipids contained therein, for example, by contact with "cold" acetone, aerosil, calcium and dextran sulfate, and the like. For instance, IV-1 paste may be mixed with acetone in the proportion of about 10–40 parts of acetone per part of Fraction IV-1. The temperature during this treatment is maintained at about −30° to −35° C., the starting temperature of the cold acetone. Acetone also removes water from Fraction IV-1 paste, thereby resulting, upon removal of the acetone by conventional means, in a dry powder containing substantially all of the PI.

Following this hold period under the conditions according to the present invention, the resulting aqueous solution of Fr. IV-1 is then treated in a conventional manner, as described by Coan et al, with a polycondensed polyalkylene glycol to precipitate unwanted proteins and to obtain a mixture containing PI free of unwanted proteins, the PI-containing mixture is recovered, and PI is separated from the recovered mixture.

Preferably, the polycondensed polyalkylene glycol is selected from polyethylene glycol (PEG) and polypropylene glycol (PPG). Although either may be used, PEG is preferred because it is more readily available, for example from Union Carbide Corp. The PEG may have a molecular weight in the range of about 200 to 20,000, preferably about 2,000–10,000, more preferably about 3,000 to 8,000, most preferably about 3,000 to 4,000, and may be used in the range of about 8 to 23% (w/v), based on amount of mucous solution. This treatment may be held at about 2° C.–50° C. for about 0.2–24 hours.

The precipitate that forms, which contains unwanted proteins, may be separated by conventional means such as centrifugation and filtration. The mixture containing PI free of unwanted proteins is recovered and then treated so as to separate PI therefrom. Alternatively, the pH of the mixture from the PEG treatment, which contains the precipitate of unwanted proteins, may be adjusted to within the range of 4.6–5.7, preferably 5.1–5.2, by the addition of a physiologically acceptable acid such as acetic acid, citric acid, hydrochloric acid, and phosphoric acid. The acidified mixture is held for as short a time as possible to further precipitate unwanted proteins from solution, usually about 1–60 minutes, because the yield of PI decreases with time under these conditions. The precipitate that forms, which contains unwanted proteins, is separated, again by conventional means.

The pH of the remaining solution is adjusted to about 5.5–8.6, preferably about 6.5, by the addition of a physiologically acceptable alkaline material such as, for example, sodium hydroxide.

The so-adjusted material is then further fractionated by the addition of PEG in the amount of 10–30 g per 100 ml of solution. A precipitate containing PI is separated from the solution. The precipitate is dissolved in a sodium phosphate buffer and the resulting solution is contacted with an anion exchange medium such as DEAE-Sephadex, QAE-Sephadex, DEAE-Sephacel, DEAE-cellulose, DEAE-Sepharose or the like. A variety of conditions may be used in this particular step. Contact with the above agent may be carried out batchwise or continuously. For best results the anion exchange medium is placed in a chromatographic column and the PI eluted therefrom. In general, the anion exchange medium is first equilibrated in a buffer solution of pH about 5.5–8.6. Next, the anion exchange medium is contacted with the above solution containing PI in the proportion of about 10–15 volumes of solution to 1 volume exchanger. The anion exchange medium is washed again with a buffer solution, usually the same buffer solution as above; the amount of this wash solution generally is about 3–10 volumes per volume of exchanger.

The PI is removed by either gradient elution or stepwise elution from the anion exchange medium by contacting it with a buffer solution of pH about 5.5–8.6 containing 0.0–0.3M sodium chloride, 0.01–0.12M disodium phosphate, and the like or combinations thereof.

Following the separation of the solution containing PI, for example, from the anion exchange medium, the solution is treated to reduce its water content and change the ionic composition by conventional means such as by diafiltration, ultrafiltration, lyophilization, etc., or combinations thereof.

The PI obtained by the method according to the present invention, as a precipitate and reconstituted in buffer solution or as a solution or concentrate thereof, can be formulated into pharmaceutical preparations containing a protease inhibitory effective amount of PI and a pharmaceutically acceptable carrier for therapeutic, diagnostic, or other uses. To prepare them for intravenous administration the compositions are dissolved usually in water containing physiologically compatible substances such as sodium chloride, glycine, and the like and having a buffered pH compatible with physiological conditions. Generally, guidelines for intravenously administered compositions are established by governmental regulations.

It is desirable that the PI concentrates be non-infective with respect to infectious microorganisms, e.g. hepatitis and AIDS viruses. In this respect the concentrates may be treated to inactivate such microorganisms and reduce infectivity to the same, for example, by one or more of sterile-filtration, ultraviolet irradiation, treatment with chemical viral inactivating agents, heat treatment (e.g. 60°–85° C.) in the lyophilized state, or "pasteurization", i.e., heating a PI-containing solution at a temperature and for a time, such as, for example, at about 60° C. or more for a period up to about 10 hours, sufficient to render the PI hepatitis non-infective. To stabilize the PI during this pasteurization, or "wet" heat treatment, a source of citrate ions is added in an amount sufficient to stabilize the PI during heating. Generally, if about 20 mg of total protein is present in the PI concentrate, then the solution is made about 0.25–0.5M in citrate ion. The pH of the mixture during this heating step should preferably be about 6.0–7.0.

To achieve maximum stabilization of PI during heating it is desirable to use a carbohydrate as the stabilization agent either alone or with sodium citrate. For this purpose one may use as the carbohydrate a mono-, di-, and trisaccharide such as arabinose, glucose, galactose, maltose, fructose, ribose, mannose, rhammose, sucrose, etc., or a sugar alcohol such as sorbitol and mannitol, etc., in an amount of about 0.5–2.4 g/ml of PI solution.

As mentioned above the pasteurized products of the invention may be incorporated into pharmaceutical preparations which may be used for therapeutic purposes. However, the term "pharmaceutical preparation" is intended in a broader sense herein to include preparations containing a protein composition in accordance with this invention used not only for therapeutic purposes, but also for reagent or diagnostic purposes as known in the art or for tissue culture. The pharmaceutical preparation intended for therapeutic use should contain a therapeutic amount of PI, i.e., that protease inhibitory amount necessary for preventative or curative health measures. If the pharmaceutical preparation is to be employed as a reagent or diagnostic, then it should contain reagent or diagnostic amounts of PI.

EXAMPLES

The invention described above is demonstrated further by the following illustrative examples.

Cohn Fraction IV-1 was obtained by means of fractionation according to the Cohn fractionation techniques mentioned above.

Assays

PI is estimated by its elastase inhibitory capacity, using a chromogenic substrate for elastase. Hydrolysis of N-succinyl-L-alanyl-L-alanyl-L-alanyl-p-nitroanilide (SA₃pNA) by elastase causes an increase in absorption at 405 nm. This increase is continuously monitored usually at 37° C. Comparisons of the linear changes of absorbance with time in the presence and absence of sample (PI) are made. The amount of inhibitor is then calculated based on the known molecular weights of elastase and PI, on the known 1:1 stoichiometry, and on the known amount of elastase used.

PI may also be estimated by its trypsin inhibitory capacity in a similar manner.

Antithrombin III. The Lowry protein assay was used using human serum albumin as the standard (Lowry et al, *J. Biol. Chem.*, 1951, Vol. 193, pages 265–275). Additionally, antithrombin concentrations were calculated from the absorbance at 280 nm using an extinction coefficient of 6.5.

EXAMPLE 1

Modifications to the Alpha-1-Proteinase Inhibitor Process

Following substantially the fractionation scheme outlined by Coan, et al, U.S. Pat. No. 4,379,087, Example 1, for the isolation of alpha-1-proteinase inhibitor, Fraction IV-1 paste was dissolved in 8 volumes of a buffer solution of pH 8.2 containing 0.1M Tris and 0.02M sodium chloride. The resulting suspension, or mixture, was stirred for 2.5 hours at 5° C., heated to 40°–45° C. and held for 1–1.5 hours, and cooled to 5° C. prior to assay. This was identified "Sample A".

In an effort to increase the solubility of alpha-1-proteinase inhibitor from Fraction IV-1, Fraction IV-1 paste was suspended in 24 volumes of 0.1M Tris, 0.02M sodium chloride, pH 8.2. As above, the resulting mixture was stirred for 2.5 hours at 5° C., heated to 40°–45° C. and held for 1–1.5 hours, and cooled to 5° C. prior to assay. This was identified "Sample B".

Experiments were performed to test the necessity for pH adjustment of the Tris/saline buffer prior to paste addition. Fraction IV-1 paste was dissolved in 24 volumes of 0.1M Tris, 0.02M sodium chloride (pH=10.3–10.5). The resulting pH after paste addition was found to be 9.3–9.5. This compares to the above 24 volume suspension which ranged from 7.7–8.0 after paste addition. The resulting mixture was stirred for 2.5 hours at 5° C., heated to 40°–45° C. and held for 1–1.5 hours, and cooled to 5° C. prior to assay. This was identified "Sample C".

These three conditions were also compared with Fraction IV-1 paste which was dissolved in 0.1M Tris, 0.02M sodium chloride with the pH maintained at 10.0–10.3 during mixing. The resulting paste suspension was stirred for 2.5 hours at 5° C., heated to and held at 30°–35° C. for 1–1.5 hours, then cooled to 5° C. prior to assay. This was identified "Sample D".

These samples, A–D, were then processed to separate PI contained therein as described above by precipitating unwanted proteins by the addition of PEG, absorbing the PI on an anion exchange resin, and eluting the PI from the anion exchange resin.

Table I below summarizes the assay results of the samples prepared as described above.

TABLE I

| | | | Assay Results | | | | | |
|---|---|---|---|---|---|---|---|---|
| Sample | Condition/ Buffer pH | Dissolved IV-1 pH | A280 | mg/ml | mg PI/ g IV-1 | % Yield in IV-1 From Pooled Plasma* | % Yield in PEG From Pooled Plasma* | Final % Yield From Pooled Plasma |
| A | 8 vol/pH 8.18 | 7.8 | 34.3 | 1.55 | 13.95 | 18.2 | 8.7 | 6.4 |
| B | 24 vol/pH 8.18 | 8.0 | 12.2 | 0.75 | 18.75 | 30.3 | 20.7 | 14.5 |
| C | 24 vol/pH 10.4 | 9.5 | 13.2 | 1.35 | 33.75 | 50.1 | 38.5 | 30.0 |
| D | 24 vol/pH 10.4 | 10.1 | 11.1 | 1.25 | 31.25 | 46.1 | ND | ND |

*1.3 g PI/L pooled plasma assumed for calculation.
ND = Not done

EXAMPLE 2

Modifications to the Antithrombin-III Process

Following substantially the procedure of C. A. Wickerhauser et al, *Vox Sang.*, 36 281 at 284 (1979) for the isolation of AT-III, Fraction IV-1 paste was dissolved in 8 volumes of a buffer solution of pH 8.2 containing 0.1M Tris and 0.02M sodium chloride. The resulting suspension, or mixture, was stirred for 2.5 hours at 5° C., heated to 40°–45° C. and held for 1–1.5 hours, and cooled to 5° C. prior to assay. This was identified "Sample E".

In an effort to increase the solubility of alpha-1-proteinase inhibitor from Fraction IV-1, Fraction IV-1 paste was suspended in 24 volumes of 0.1M Tris, 0.02M sodium chloride, pH 8.2. As above, the resulting mixture was stirred for 2.5 hours at 5° C., heated to 40°–45° C. and held for 1–1.5 hours, and cooled to 5° C. prior to assay. This was identified "Sample F".

Experiments were performed to test the necessity for pH adjustment of the Tris/saline buffer prior to paste addition. Fraction IV-1 paste was dissolved in 24 volumes of 0.1M Tris, 0.02M sodium chloride (pH=10.3–10.5). The resulting pH after paste addition was found to be 9.3–9.5. This compares to the above 24 volume suspension which ranged from 7.7–8.0 after paste addition. The resulting mixture was stirred for 2.5 hours at 5° C., heated to 40°–45° C. and held for 1–1.5 hours, cooled to 5° C., and the pH adjusted to 7.5–8.0 prior to assay. This was identified "Sample G".

These three conditions were also compared with Fraction IV-1 paste which was dissolved in 0.1M Tris, 0.02M sodium chloride with the pH maintained at 10.0–10.3 during mixing. The resulting paste suspension was stirred for 2.5 hours at 5° C., heated to and held at 30°-35° C. for 1–1.5 hours, then cooled to 5° C., and the pH adjusted to 7.5–8.0 prior to assay. This was identified "Sample H".

Table II below summarizes the assay results of the samples prepared as described above.

TABLE II

Assay Results

| Sample | Condition/ Buffer pH | Dissolved IV-1 pH | A280 | units/ ml | units AT-III/ g IV-1 | % Yield in IV-1 From Pooled Plasma* |
|---|---|---|---|---|---|---|
| E | 8 vol/ pH 8.18 | 7.8 | 32.5 | 0.98 | 8.8 | 15.2 |
| F | 24 vol/ pH 8.18 | 8.0 | 12.3 | 0.84 | 21.0 | 39.3 |
| G | 24 vol/ pH 10.4 | 9.5 | 13.5 | 1.02 | 25.5 | 45.0 |
| H | 24 vol/ pH 10.4 | 10.1 | 12.8 | 1.08 | 27.0 | 41.0 |

*1.0 Unit AT-III/L Pooled Plasma assumed for calculation.

What is claimed is:

1. A method for separating one of alpha-1-proteinase inhibitor and antithrombin-III from an aqueous solution of plasma proteins containing at least one of alpha-1-proteinase inhibitor and antithrombin-III which comprises the steps of:
    (a) providing a solution of the group of blood plasma and blood plasma fraction containing at least one of alpha-1-proteinase inhibitor and antithrombin-III dissolved in from 20 to 100 volumes of physiologically compatible buffer solution per weight of the one of the plasma and plasma fraction used;
    (b) adjusting the pH of the resulting solution from step (a) to from 9.0 to 11.0; and
    (c) separating at least one of the alpha-1-proteinase inhibitor and antithrombin-III from the solution from step (b) by contacting the solution from step (b) with one of a precipitating agent and an adsorbing agent.

2. In a method for separating antithrombin-III from an aqueous solution of plasma proteins containing antithrombin-III which comprises the steps of:
    (a) contacting an aqueous solution of one of the group of blood plasma and a blood plasma fraction which contains antithrombin-III with a water-insoluble, cross-linked sulfated polysaccharide gel matrix adsorbing agent to adsorb antithrombin-III,
    (b) eluting antithrombin-III from the adsorbing agent from step (a), and
    (c) recovering antithrombin-III from the eluant from step (b),
the improvement which comprises:
    (1) providing for use in step (a) an aqueous solution of the one of the blood plasma and blood plasma fraction dissolved in from 20 to 100 volumes of buffer-solution per weight of the plasma or plasma fraction used, and
    (2) prior to use in step (a), adjusting one of the buffer solution and the resulting aqueous solution of the blood plasma and blood plasma fraction from step (1) to render the pH of the resulting solution at from 9.0 to 11.0.

3. In a method for separating alpha-1-proteinase inhibitor from an aqueous solution of plasma proteins containing alpha-1-proteinase inhibitor which comprises the steps of:
    (a) contacting an aqueous solution of one of the group of blood plasma and a blood plasma fraction containing alpha-1-proteinase inhibitor with from about 8% to about 23% (w/v), based on volume of the aqueous solution, of a polycondensed polyalkylene glycol selected from polyethylene glycol and polypropylene glycol, at a temperature of from about 2° C. to about 50° C. for a period of about 0.2–24 hours to selectively precipitate unwanted proteins from the solution without precipitating alpha-1-proteinase inhibitor to obtain a mixture containing alpha-1-proteinase inhibitor free of unwanted proteins,
    (b) recovering the mixture from step (a), and
    (c) separating alpha-1-proteinase inhibitor from the mixture recovered in step (b),
the improvement which comprises the steps of:
    (1) providing for use in step (a) an aqueous solution of the one of the blood plasma and blood plasma fraction dissolved in from 20 to 100 volumes of the buffer solution per weight of the one of the plasma and plasma fraction used, and
    (2) adjusting the pH of one of the buffer solution and the resulting aqueous solution of the blood plasma and blood plasma fraction to render the pH of the resulting solution at from 9.0 to 11.0.

4. A method according to claim 3 wherein the aqueous solution of plasma proteins containing alpha-1-proteinase inhibitor is selected from the group of plasma fractions consisting of Cohn Fraction IV-1, Cohn Fraction IV, reworks of Cohn Fraction IV and IV-1, Cohn Effluent II+III, Cohn Effluent I, and cryosupernatant solution.

5. A method according to claim 3 wherein the aqueous solution of plasma proteins containing alpha-1-proteinase inhibitor is selected from the group consisting of Cohn Fraction IV-1, Cohn Fraction IV, Cohn Effluent II+III and Cohn Effluent I.

6. A method according to claim 3 wherein the aqueous solution of plasma proteins containing alpha-1-proteinase inhibitor is Cohn Fraction IV-1.

7. A method according to claim 3 wherein in the improvement step (1) there is used from 20 to 50 volumes of buffer solution per weight of the one of the plasma and plasma fraction.

8. A method according to claim 3 wherein in the improvement step (1) there is used from 20 to 30 volumes of buffer solution per weight of the one of the plasma and plasma fraction.

9. A method according to claim 3 wherein in the improvement step (1) there is used 24 volumes of buffer solution per weight of the one of the plasma and plasma fraction.

10. A method according to claim 7 wherein the pH of the one of the buffer solution and the resulting aqueous solution is adjusted to render the pH of the resulting solution from 9.0 to 10.5.

11. A method according to claim 8 wherein the pH of the one of the buffer solution and the resulting aqueous solution is adjusted to render the pH of the resulting solution from 9.0 to 10.5.

12. A method according to claim 9 wherein the pH of the one of the buffer solution and the resulting aqueous solution is adjusted to render the pH of the resulting solution from 9.0 to 10.5.

13. A method according to claim 1 including the further step of treating at least one of alpha-1-proteinase inhibitor and an anticoagulant effective amount of antithrombin-III obtained from step (c) to inactivate, and to reduce the infectivity of, infectious microorganisms so as to render the alpha-1-proteinase inhibitor non-infectious to such infectious microorganisms and thereby render the alpha-1-proteinase inhibitor useful for therapeutic and prophylactic purposes.

14. A method for separating one of alpha-1-proteinase inhibitor and antithrombin-III from an aqueous solution of plasma proteins containing at least one of alpha-1-proteinase inhibitor and antithrombin-III which comprises the steps of:
   (a) providing a solution of the group of blood plasma and blood plasma fraction containing at least one of alpha-1-proteinase inhibitor and antithrombin-III dissolved in from 20 to 100 volumes of physiologically compatible buffer solution per weight of the one of the plasma and plasma fraction used; and
   (b) separating at least one of the alpha-1-proteinase inhibitor and antithrombin-III from the solution from step (a) by contacting the solution from step (a) with one of a precipitating agent and an adsorbing agent.

15. In a method for separating antithrombin-III from an aqueous solution of plasma proteins containing antithrombin-III which comprises the steps of:
   (a) contacting an aqueous solution of one of the group of blood plasma and a blood plasma fraction which contains antithrombin-III with a water-insoluble, cross-linked sulfated polysaccharide gel matrix adsorbing agent to adsorb antithrombin-III,
   (b) eluting antithrombin-III from the adsorbing agent from step (a), and
   (c) recovering antithrombin-III from the eluant from step (b),
the improvement which comprises:
   (1) providing for use in step (a) an aqueous solution of the one of the blood plasma and blood plasma fraction dissolved in from 20 to 100 volumes of buffer-solution per weight of the plasma or plasma fraction used.

16. In a method for separating alpha-1-proteinase inhibitor from an aqueous solution of plasma proteins containing alpha-1-proteinase inhibitor which comprises the steps of:
   (a) contacting an aqueous solution of one of the group of blood plasma and a blood plasma fraction containing alpha-1-proteinase inhibitor with from about 8% to about 23% (w/v), based on volume of the aqueous solution, of a polycondensed polyalkylene glycol selected from polyethylene glycol and polypropylene glycol, at a temperature of from about 2° C. to about 50° C. for a period of about 0.2–24 hours to selectively precipitate unwanted proteins from the solution without precipitating alpha-1-proteinase inhibitor to obtain a mixture containing alpha-1-proteinase inhibitor free of unwanted proteins,
   (b) recovering the mixture from step (a), and
   (c) separating alpha-1-proteinase inhibitor from the mixture recovered in step (b),
the improvement which comprises the steps of:
   (1) providing for use in step (a) an aqueous solution of the one of the blood plasma and blood plasma fraction dissolved in from 20 to 100 volumes of the buffer solution per weight of the one of the plasma and plasma fraction used.

17. A method according to claim 16 wherein the aqueous solution of plasma proteins containing alpha-1-proteinase inhibitor is selected from the group of plasma fractions consisting of Cohn Fraction IV-1, Cohn Fraction IV, reworks of Cohn Fraction IV and IV-1, Cohn Effluent II+III, Cohn Effluent I, and cryosupernatant solution.

18. A method according to claim 16 wherein the aqueous solution of plasma proteins containing alpha-1-proteinase inhibitor is selected from the group consisting of Cohn Fraction IV-1, Cohn Fraction IV, Cohn Effluent II+III and Cohn Effluent I.

* * * * *